(12) United States Patent
Helmer

(10) Patent No.: US 10,918,798 B2
(45) Date of Patent: Feb. 16, 2021

(54) MEDICAMENT INJECTION DEVICE

(71) Applicant: Sanofi-Aventis Deutschland GMBH, Frankfurt a m Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 233 days.

(21) Appl. No.: 15/778,428

(22) PCT Filed: Nov. 21, 2016

(86) PCT No.: PCT/EP2016/078258
§ 371 (c)(1),
(2) Date: May 23, 2018

(87) PCT Pub. No.: WO2017/089269
PCT Pub. Date: Jun. 1, 2017

(65) Prior Publication Data
US 2018/0353695 A1    Dec. 13, 2018

(30) Foreign Application Priority Data
Nov. 27, 2015 (EP) .................................... 15196689

(51) Int. Cl.
*A61M 5/24*    (2006.01)
*A61M 5/32*    (2006.01)
(Continued)

(52) U.S. Cl.
CPC .......... *A61M 5/2466* (2013.01); *A61M 5/288* (2013.01); *A61M 5/3202* (2013.01);
(Continued)

(58) Field of Classification Search
CPC ........ A61M 5/2466; A61M 2005/2474; A61M 5/288; A61M 5/3146
See application file for complete search history.

(56) References Cited

U.S. PATENT DOCUMENTS

| 3,825,003 A | * | 7/1974 | Kruck | ................... A61M 5/288 604/192 |
| 5,928,205 A | | 7/1999 | Marshall | |

(Continued)

FOREIGN PATENT DOCUMENTS

| EP | 0990446 | 4/2000 |
| GB | 1151222 | 5/1969 |

(Continued)

OTHER PUBLICATIONS

PCT International Preliminary Report on Patentability in International Appln. No. PCT/EP2016/078258, dated May 29, 2018, 8 pages.

(Continued)

*Primary Examiner* — Emily L Schmidt
(74) *Attorney, Agent, or Firm* — Fish & Richardson P.C.

(57) ABSTRACT

A medicament injection device includes a main body configured to receive a medicament cartridge sealed by a penetrable barrier, a cap assembly having an inner needle part and an outer needle part, wherein the inner needle part is movable in a proximal direction with respect to the outer needle part, a needle carrier carrying a needle, the needle carrier being releasably coupled to the inner needle part, wherein, when the inner needle part is displaced in the proximal direction, the inner needle part causes the needle carrier to be displaced axially in the proximal direction, and wherein, subsequent to the axial displacement of the inner needle part, the cap assembly is separable from the main body by movement of the cap assembly in a distal direction.

15 Claims, 5 Drawing Sheets

(51) Int. Cl.
*A61M 5/28* (2006.01)
*A61M 5/20* (2006.01)
*A61M 5/31* (2006.01)

(52) U.S. Cl.
CPC .......... *A61M 5/3204* (2013.01); *A61M 5/326* (2013.01); *A61M 5/2033* (2013.01); *A61M 2005/208* (2013.01); *A61M 2005/2013* (2013.01); *A61M 2005/2474* (2013.01); *A61M 2005/3117* (2013.01); *A61M 2005/3267* (2013.01); *A61M 2205/18* (2013.01); *A61M 2205/3306* (2013.01); *A61M 2205/581* (2013.01); *A61M 2205/583* (2013.01)

(56) References Cited

U.S. PATENT DOCUMENTS

2003/0144633 A1     7/2003    Kirchhofer

2011/0224640 A1*   9/2011    Kuhn ................... B65D 51/002
                                                             604/414
2011/0276008 A1*   11/2011    Matthias ................ A61M 5/34
                                                             604/201
2014/0249480 A1*   9/2014    Mercer ............... A61M 5/2448
                                                             604/198

FOREIGN PATENT DOCUMENTS

| WO | WO 96/30065 | 10/1996 |
| WO | WO 97/36624 | 10/1997 |
| WO | WO 2010/022870 | 3/2010 |
| WO | WO 2012/089821 | 7/2012 |

OTHER PUBLICATIONS

PCT International Search Report and Written Opinion in International Appln. No. PCT/EP2016/078258, dated Jan. 2, 2017, 11 pages.

* cited by examiner

MEDICAMENT INJECTION DEVICE

CROSS REFERENCE TO RELATED APPLICATIONS

The present application is the national stage entry of International Patent Application No. PCT/EP2016/078258, filed on Nov. 21, 2016, and claims priority to Application No. EP 15196689.2, filed in on Nov. 27, 2015, the disclosures of which are expressly incorporated herein in entirety by reference thereto.

TECHNICAL FIELD

The present disclosure relates to medicament injection devices.

BACKGROUND

Medicament injection devices can take various forms. One form uses a syringe, where medicament is stored in a hollow cylinder, typically formed of glass. The medicament is sealed from the environment with a plunger moveable within the cylinder, and a needle fluidly connected to the syringe's distal end. The needle must remain capped in order to maintain the medicament under sterile conditions.

Another form of injection device uses a cartridge instead of a syringe, the cartridge having a distal seal instead of the syringe's needle. Typically a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection. The injection device described herein aims to overcome one or more problems associated with prior devices.

SUMMARY

A first embodiment provides a medicament injection device comprising a main body configured to receive a medicament cartridge sealed by a penetrable barrier; a cap assembly having an inner needle part and an outer needle part, wherein the inner needle part is movable in a proximal direction with respect to the outer needle part, a needle carrier carrying a needle, the needle carrier being releasably coupled to the inner needle part, wherein, when the inner needle part is displaced in the proximal direction, the inner needle part causes the needle carrier to be displaced axially in the proximal direction; and wherein, subsequent to the axial displacement of the inner needle part, the cap assembly is separable from the main body by movement of the cap assembly in a distal direction.

The device may further comprise a medicament cartridge holder for holding the medicament cartridge, the medicament cartridge holder having a needle carrier support part having a distal flange to support the needle carrier away from the medicament cartridge before displacement of the needle carrier and adapted to fix the needle carrier to the medicament cartridge subsequent to axial displacement of the needle carrier.

The needle carrier may have a circumferential groove and the needle carrier support part may have a flange arranged to engage with the groove so that the needle holder is held away by an axial separation from the medicament cartridge prior to displacement of the needle carrier.

The needle sleeve may be coupled to the cap assembly by a frictional fit.

The outer needle part may have a ridge arranged to abut a flange of the needle sleeve so that movement of the cap assembly in a distal direction is prevented prior to displacement of the inner needle part in a proximal direction.

The inner needle part may have a reinforcing flange for reinforcing the outer needle part against the needle sleeve.

Proximal and distal ends of the needle may each be stored in respective substantially airtight compartments prior to proximal displacement of the inner needle part.

A distal end of the inner needle part may have a tapered part that is arranged to engage with the outer needle part subsequent to the axial displacement of the inner needle part in a proximal direction.

The tapered part may be dimensioned so as to provide an audible feedback as the inner needle part is moved in a proximal direction.

The inner needle part may comprise a shaded region to provide a visual indication to a user that the needle has not been inserted into the medicament cartridge.

The inner needle part may have a transparent needle inspection portion.

The device may contain a medicament cartridge sealed by a penetrable barrier, wherein proximal axial movement of the needle carrier causes a proximal end of the needle to pierce the penetrable barrier.

The medicament cartridge may contain a medicament.

The device may be an auto-injector device.

A second embodiment provides a method of operating a medicament injection device having a cap with a push button, the method comprising pushing the push button in a proximal axial direction, thereby causing a needle to pierce a penetrable barrier of a medicament cartridge; and pulling the cap in a distal axial direction to remove the cap from the device.

BRIEF DESCRIPTION OF THE DRAWINGS

Exemplary embodiments of the present disclosure are described with reference to the accompanying drawings, in which.

DETAILED DESCRIPTION

Figure 1:
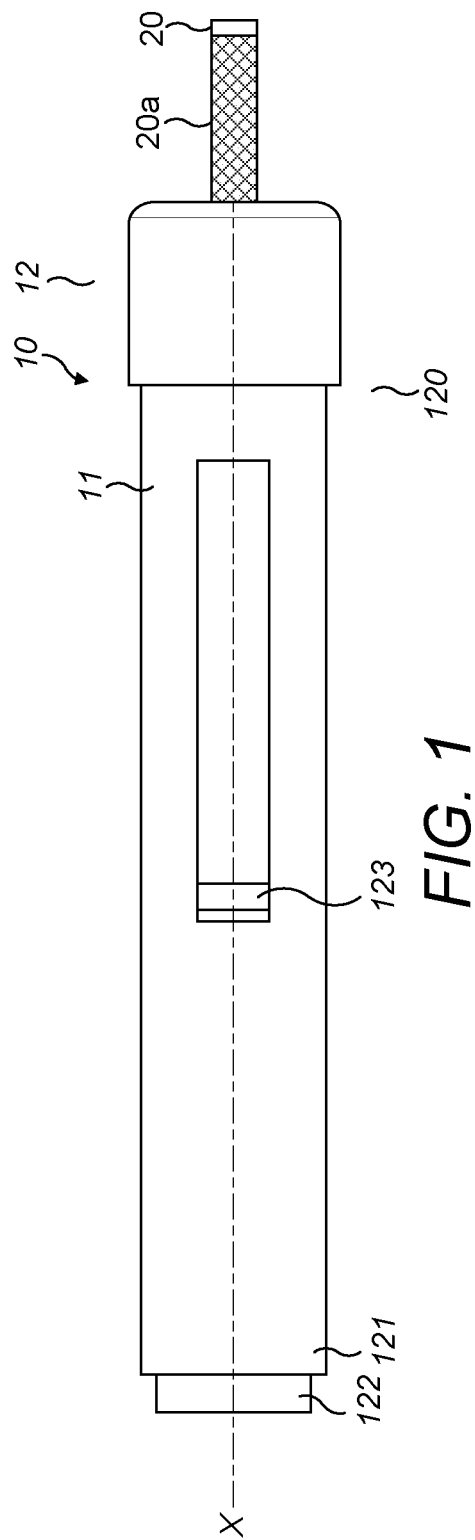
FIG. 1 is a side-on view of an auto-injector device according to an embodiment of the disclosure.

Embodiments of the present disclosure provide a mechanism for inserting a needle of an injection device into a cartridge containing a medicament for injection by a patient or care giver. The mechanism allows the medicament cartridge to remain sealed until such time as the user wishes to commence the injection. Automating a mechanism for inserting the needle into the medicament cartridge also reduces the amount of handling of the needle by the user prior to the injection. Indeed, in some embodiments described below, the user does not touch the needle when the needle is inserted into the medicament cartridge.

In embodiments of the disclosure the needle is initially coupled to a cap of the device and is isolated from the sealed medicament cartridge during storage (i.e. after manufacture and before use). By pushing the cap, the user causes the needle to become fixed to the medicament cartridge and to disengage from the cap. The cap can then be removed. As a result, the needle is in fluid communication with medicament and the injection may be commenced.

The steps of storing the device and subsequently inserting the needle into the medicament cartridge can be performed without exposing the needle.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIG. 1. Device 10, as described above, is configured to inject a medicament into a patient's body. Device 10 includes a main body 11 which typically contains a reservoir containing the medicament to be injected (e.g., a syringe) and the components required to facilitate one or more steps of the delivery process. Device 10 can also include a cap assembly 12 that can be detachably mounted to the main body 11. Typically a user must remove cap 12 from main body 11 before device 10 can be operated.

As shown, main body 11 is substantially cylindrical and has a substantially constant diameter along the longitudinal axis X. The main body 11 has a distal region 120 and a proximal region 121. The term "distal" refers to a location that is relatively closer to a site of injection, and the term "proximal" refers to a location that is relatively further away from the injection site.

Device 10 can also include a needle sleeve 24 (see FIG. 2C) coupled to main body 11 to permit movement of sleeve 24 relative to main body 11. For example, sleeve 24 can move in a longitudinal direction parallel to longitudinal axis X. Specifically, movement of sleeve 24 in a proximal direction can permit a needle 17 to extend from distal region 120 of main body 11.

Insertion of needle 17 into an injection site can occur via several mechanisms. For example, needle 17 may be fixedly located relative to main body 11 and initially be located within an extended needle sleeve 24. Proximal movement of sleeve 24 by placing a distal end of sleeve 24 against a patient's body and moving main body 11 in a distal direction will uncover the distal end of needle 17. Such relative movement allows the distal end of needle 17 to extend into the patient's body. Such insertion is termed "manual" insertion as needle 17 is manually inserted via the patient's manual movement of main body 11 relative to sleeve 24.

Another form of insertion is "automated," whereby needle 17 moves relative to main body 11. Such insertion can be triggered by movement of sleeve 24 or by another form of activation, such as, for example, a button 122. As shown in FIG. 1, button 122 is located at a proximal end of main body 11. However, in other embodiments, button 122 could be located on a side of main body 11.

Other manual or automated features can include drug injection or needle retraction, or both. Injection is the process by which a bung or piston 123 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of main body 11, and a distal end of the drive spring can be configured to apply a compressive force to a proximal surface of piston 123. Following activation, at least part of the energy stored in the drive spring can be applied to the proximal surface of piston 123. This compressive force can act on piston 123 to move it in a distal direction. Such distal movement acts to compress the liquid medicament within the syringe, forcing it out of needle 17.

Following injection, needle 17 can be retracted within sleeve 24 or main body 11. Retraction can occur when sleeve 24 moves distally as a user removes device 10 from a patient's body. This can occur as needle 17 remains fixedly located relative to main body 11. Once a distal end of sleeve 24 has moved past a distal end of needle 17, and needle 17 is covered, sleeve 24 can be locked. Such locking can include locking any proximal movement of sleeve 24 relative to main body 11.

Another form of needle retraction can occur if needle 17 is moved relative to main body 11. Such movement can occur if the syringe within main body 11 is moved in a proximal direction relative to housing 11. This proximal movement can be achieved by using a retraction spring (not shown), located in distal region 120. A compressed retraction spring, when activated, can supply sufficient force to the syringe to move it in a proximal direction. Following sufficient retraction, any relative movement between needle 17 and main body 11 can be locked with a locking mechanism. In addition, button 122 or other components of device 10 can be locked as required.

Embodiments provide a cap-triggered piercing unit or rather a method for auto-injectors where a needle will be connected to a cartridge when the user activates a button on a needle cap prior to the cap being removed (before injection or using the device).

The arrangement provides needle safety and seals the sterilised needle against environmental conditions.

The user is unable to remove the cap before the button has been pushed and the piercing procedure is carried out. The cap will be released by the mechanism when the needle has reached its end position.

Figure 2A:
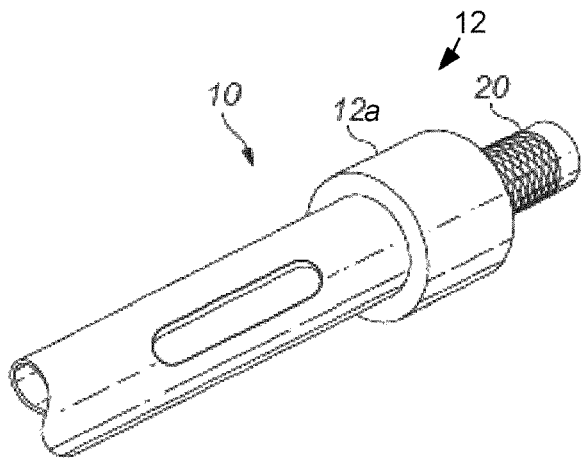
FIGS. 2A-C are perspective views of the auto-injector device of FIG. 1 in different stages of use.

FIG. 2A shows a device 10 in its original state. This is the state of the device after it has been assembled and packaged. The device 10 is in this state when the user removes the device 10 from the package. The device 10 has a cap 12. The cap 12 has a push button 20. The push button 20 has a shaded area 20a which provides a visual indication to a user that the push button 20 has to be pushed before the cap 12 can be removed and the injection commenced. For example, the shaded area 20a may be coloured red.

Figure 2B:
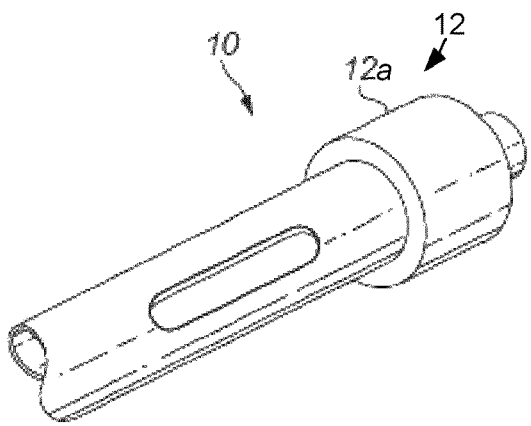

FIG. 2B shows the device 10 after the push button 20 has been pressed by the user. The shaded area 20a is no longer visible. This provides a visual indication to the user that the cap 12 may be removed. In some embodiments, an audible indication may also be provided as described in more detail below.

Figure 2C:
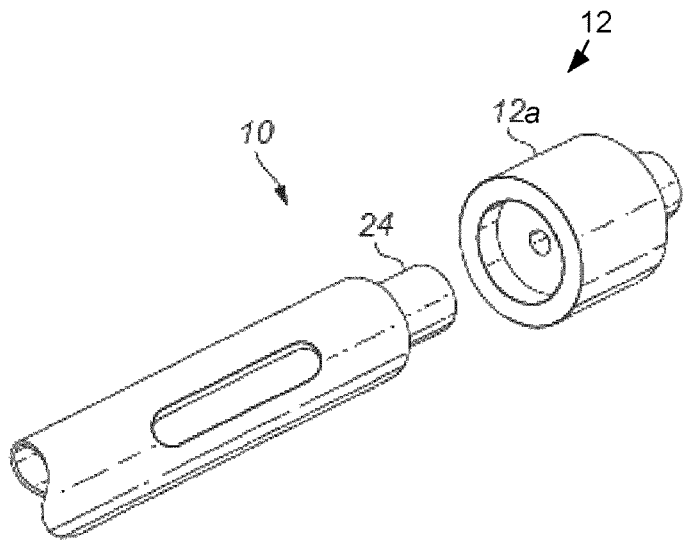

FIG. 2C shows the device 10 after the cap 12 has been removed. The needle 17 has been inserted into the medicament cartridge 19. The needle 17 is not visible in FIG. 2C because the needle sleeve 24 is obstructing the view of the needle 17.

Figure 3:
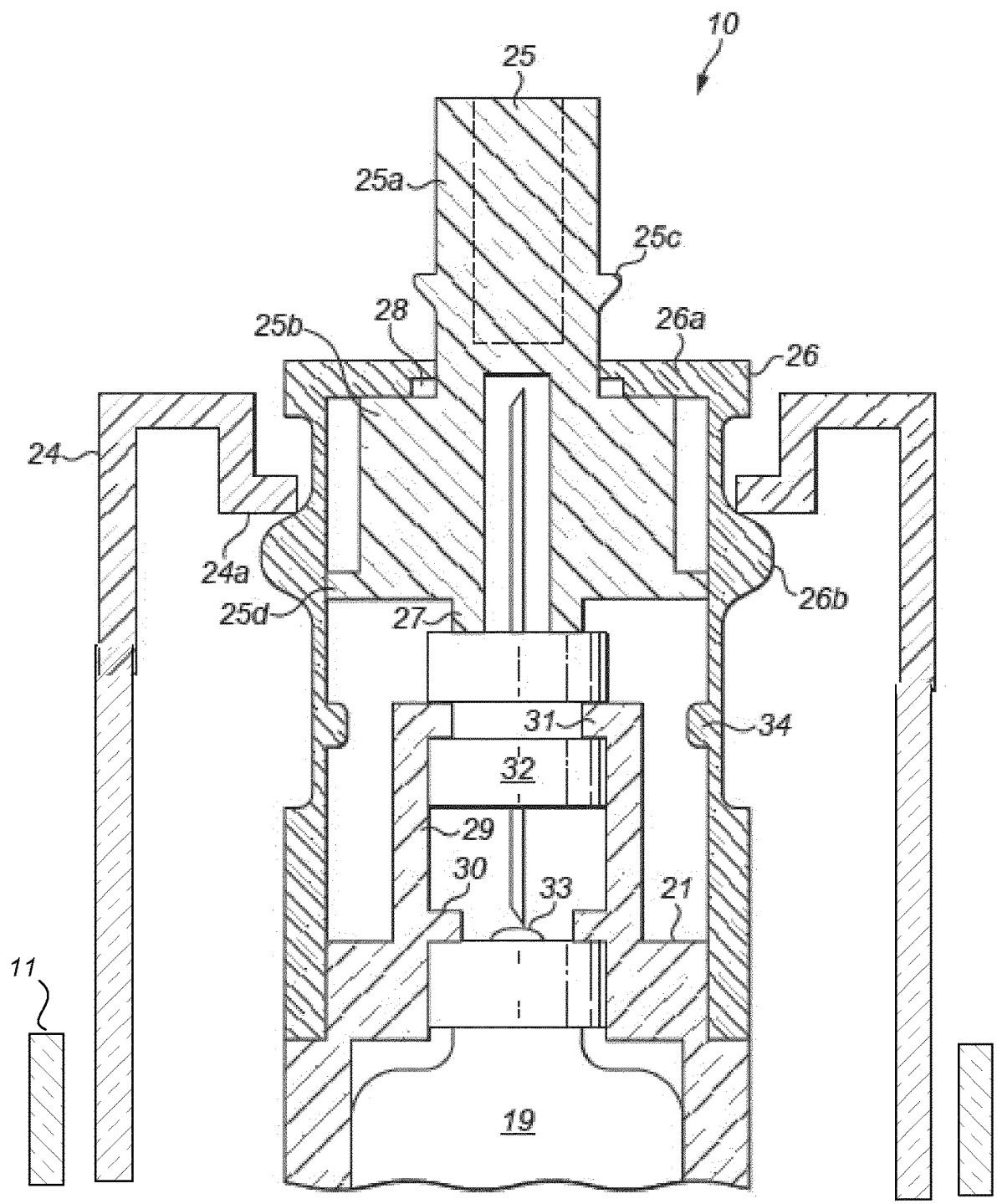
FIG. 3 is a cross sectional view of elements of the distal end of the auto-injector device at the stage shown in FIG. 2A.

FIG. 3 shows a cross section of the distal end of a device 10 according to one embodiment of the disclosure. The cap 12 is a multi-component cap assembly comprising an inner needle part 25 and an outer needle part 26. The cap 12 has a main skirt portion 12a that is fixed with respect to the outer needle part 26 and fits over the distal end of the device 10. The main skirt portion 12a of the cap 12 is not shown in FIGS. 3 and 4 to simplify the illustration. The inner needle part 25 and the outer needle part 26 are housed within the skirt portion 12a and are removed along with the rest of the cap 12 as the cap 12 is removed subsequent to the push button 20 being pushed.

The inner needle part 25 has a distal end portion 25a located at the distal end thereof and a proximal end portion 25b. The distal end portion 25a and the proximal end portion are both substantially cylindrical. The proximal end portion 25b of the inner needle part 25 is wider than the distal portion 25a and may have a diameter approximately equal to the diameter of the medicament cartridge 19. The proximal end portion 25b of the inner needle part 25 has a bore extending at least partly therethrough in an axial direction for receiving the distal end of the needle 17 during the storage stage of the device 10. The bore provides a substantially airtight compartment for the distal end of the needle 17.

As shown in FIG. 3, the distal end portion 25a protrudes axially in a distal direction from the outer needle part 26. The distal end portion 25a forms the push button 20 which is pushed by the user so that the needle 17 is inserted into the medicament cartridge 19.

Both ends of the needle 17 are sharp (i.e., needle 17 is a double-ended or double-tipped needle). The distal end of the needle is sufficiently sharp to penetrate the patient's skin during the injection. The proximal end is sufficiently sharp to allow penetration of the cartridge septum 26. The sharpness of proximal end of the needle 17 influences the piercing activation force which is required for the proximal end of the needle 17 to pierce the cartridge septum 26. In embodiments of the disclosure, the activation force is lower than 19 Newtons.

The inner needle part 25 is axially movable relative to the outer needle part 26. The distal end portion 25a thus forms the push button 20 shown in FIG. 2. A portion of the outer surface of the distal end portion 25a of the inner needle part 25 may be shaded, for example coloured red, to provide an indication to a user that they need to push the push button 20 to activate the device 10.

The distal end portion 25a of the inner needle part 25 is provided with a tapered ridge 25c. The tapered ridge 25c has a square edge facing the distal end of the device 10, substantially perpendicular to the main wall of the distal end portion 25a. The tapered ridge 25c has an oblique edge arranged to allow the tapered edge 25c to pass through an aperture in a distal end wall 26a of the outer needle part 26. The square edge is arranged to sit in a rebated portion 28 of the distal end wall 26a of the outer needle part 26 subsequent to the user pushing the push button 20. The tapered ridge 25c could be a protrusion or an indentation to receive the part 26a.

The proximal end portion 25b may have an annular base part 27 at the proximal end of the proximal end portion 25b which is arranged to abut against the needle carrier prior to removal of the cap 12. The annular base part 27 further acts to seal the distal end of the needle 17 during the storage stage of the device.

The proximal end portion 25b has a reinforcing lip 25d which abuts the outer needle part 26.

The inner needle part 25 may be transparent so that, during assembly, a camera may be used to check that the needle 17 is in the correct position. The camera may be connected to an alarm so that an alert is raised if the needle is detected to be out of position during device assembly.

The outer needle part 26 is a generally tubular element. The proximal end of the outer needle part 26 fits over a cartridge holder 21. The outer needle part 26 is removable from the cartridge holder 21. The distal end of the outer needle part 26 is provided with a distal end wall 26a having an aperture therein through which the distal end portion 25a of the inner needle part 25 emerges during the storage phase. The inner face of the distal end wall 26a is provided with a rebated section 28 to receive the tapered ridge 25c located on the distal portion 25a of the inner needle part 25 after the push button 20 is pushed by the user.

The outer needle part 26 has an outer circumferential ridge 26b arranged to abut against an inwardly extending flange 24a of the needle sleeve 24. The abutment between the outer circumferential ridge 26b and the flange provided on the needle sleeve 24 serves to help prevent unintended removal of the cap 12 from the device 10 before piercing is successful carried out. The reinforcing lip 25d abuts the inner wall of the outer needle part 26 in the vicinity of the circumferential ridge 26b when the inner needle part is in the position is shown in FIG. 3. The reinforcing lip 25d serves to reinforce the outer needle part 26 causing it to prevent any lateral disengagement between the circumferential ridge 26b and the flange 24a of the needle sleeve 24. This provides sufficient resistance to prevent accidental removal of the cap prior to the user pushing the distal end portion 25a of the inner needle part 25.

The device 10 comprises a needle sleeve 24 which is a protective sleeve that prevents unwanted exposure of the needle 17. The needle sleeve 24 has a generally similar shape to the main body and is generally tubular. The needle sleeve 24 fits inside the main body 11.

The cartridge 19 is held in place by the cartridge holder 21. The cartridge holder 21 has generally the same profile as the cartridge 19 so that the cartridge 19 is held in place. Various ways of holding the cartridge 19 may be used in accordance with the state of the art e.g. Solostar. For example, four or three ribs may be used for radial fixation of the cartridge 19. Alternatively, the cartridge 19 may be fixed axially. The cartridge holder 21 has a generally tubular needle carrier support part 29 extending axially from a distal end of the medicament cartridge 19. Each of the proximal and distal ends of the needle carrier support part 29 has a proximal flange 30 and a distal flange 31, respectively extending radially inwardly from a curved side wall of needle carrier support part 29. The distal flange 31 is arranged to support the needle carrier during the storage phase of the device 10. The distal flange 31 may be rounded.

The distal flange 31 is received by a circumferential groove in the outer surface of the body of the needle carrier.

The proximal flange 30 provides a seal between the edge of the medicament cartridge 19 and the interior of the needle carrier support part 29, thereby helping to ensure the sterility of the proximal end of the needle 17.

The needle 17 is held in place by a needle carrier 32. The needle carrier 32 is substantially cylindrical and has a passage extending axially there through to connect the distal and proximal ends of the needle 17. The central portion of the outer surface of the needle carrier 32 comprises a circumferential groove for receiving the distal flange 31 of the needle carrier support part 29 during the storage phase of the device. The space defined by the cartridge 19, the needle carrier support part 29, and the needle carrier 32 forms a substantially airtight compartment for the proximal end of the needle 17.

The medicament cartridge 19 is provided with a penetrable barrier such as a septum 33 across the distal end thereof. In the storage phase of the device, the medicament stored in the cartridge 19 is substantially sealed.

Figure 4:
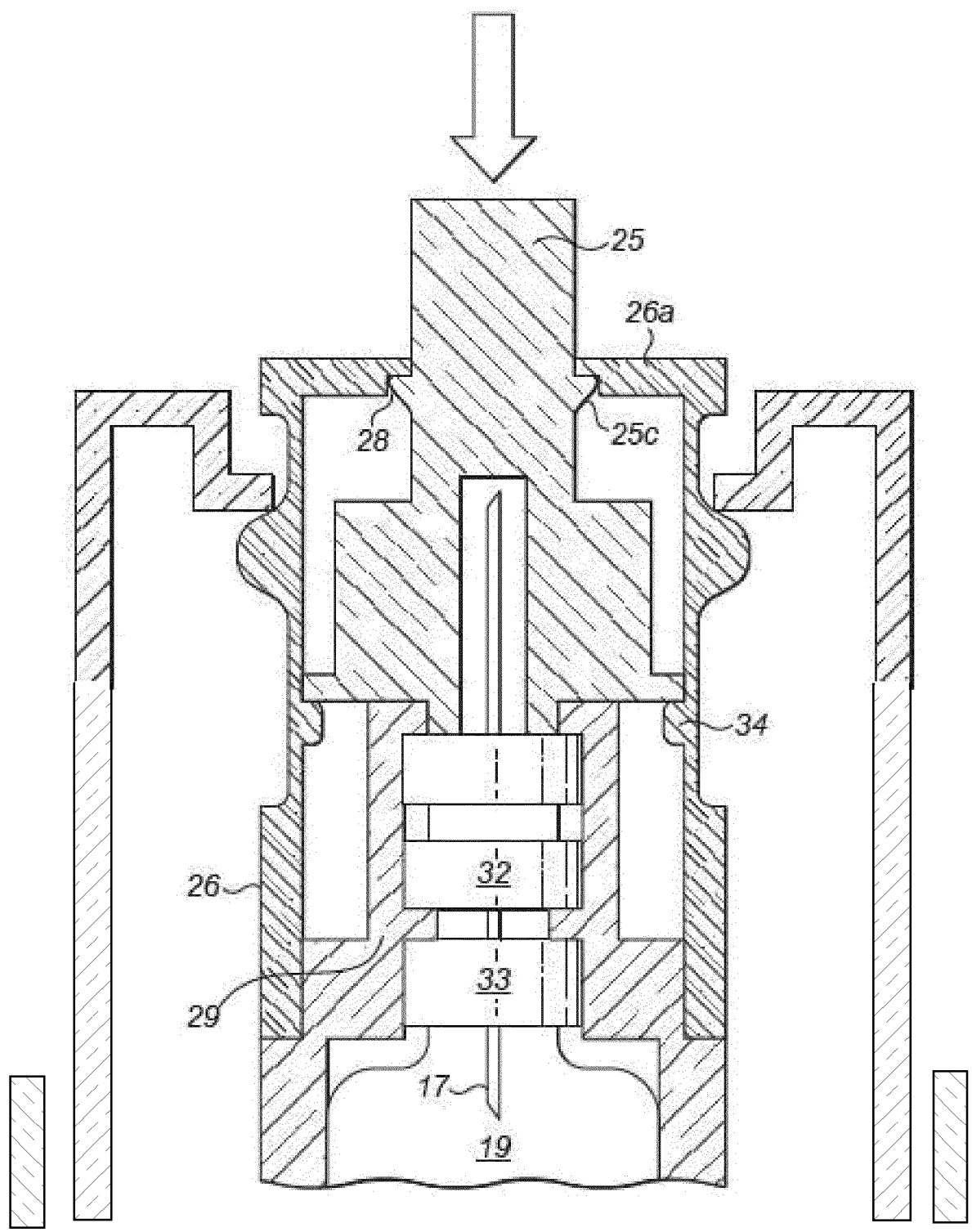
FIG. 4 is a cross sectional view of elements of the distal end of the auto-injector device at the stage shown in FIG. 2B.

FIG. 4 shows a cross section of the distal end of the device after the user has pushed the push button 20. The user pushes the push button 20, i.e. the distal end of the inner needle part 25, causing the inner needle part 25 to move axially towards the medicament cartridge 19 in the direction of the bold arrow shown in FIG. 4. The tapered leading edge of tapered ridge 25c is pushed past the distal end wall 26a of the outer needle part 26. The square edge of the tapered ridge 25c sits in the rebated portion 28 of the outer needle part 26. The engagement between the tapered ridge 25c and the rebated portion 28 ensures that both the inner needle part 25 and the outer needle part 26 of the cap assembly are removed when the user subsequently pulls the cap 12 to separate it from the rest of the device 10. As the tapered ridge moves past the distal end wall of the outer needle part 26 audible feedback may be provided to the user indicating that the cap 12 is ready to be removed.

The axial movement of the inner needle part 25 causes the needle carrier 32 to move axially towards the medicament cartridge 19. The proximal end of the needle 17 is caused to pierce the septum 33 of the medicament cartridge 19. The needle carrier support part 29 is bent 35 slightly to allow the needle carrier 32 to fit through the distal flange 31. The needle carrier 32 abuts the medicament cartridge 19. The distal flange 31 sits over the distal end of the needle carrier 32. The needle carrier 32 is thus fixed in place and subsequent substantial axial movement of the needle carrier with respect to the medicament cartridge 19 is prevented. As such, the needle carrier support part 29 helps to fix the needle carrier 32 relative to the medicament cartridge 19.

The proximal end wall of the inner needle part 25 sits against a locking ring 34 provided on the inner surface of the curved wall of the outer needle part 26. A subsequent attempt to remove the cap 12 by the user leads to the locking ring 34 engaging with the inner needle part 25 so that both the inner needle part 25 and the outer needle part 26 are removed together.

The reinforcing lip 25d is no longer proximate to the circumferential ridge 26b so that, as the user pulls the cap, the resistance between the outer needle part 26 and the needle sleeve 24 can be overcome, allowing for separation of the cap from the rest of the device.

Figure 5:
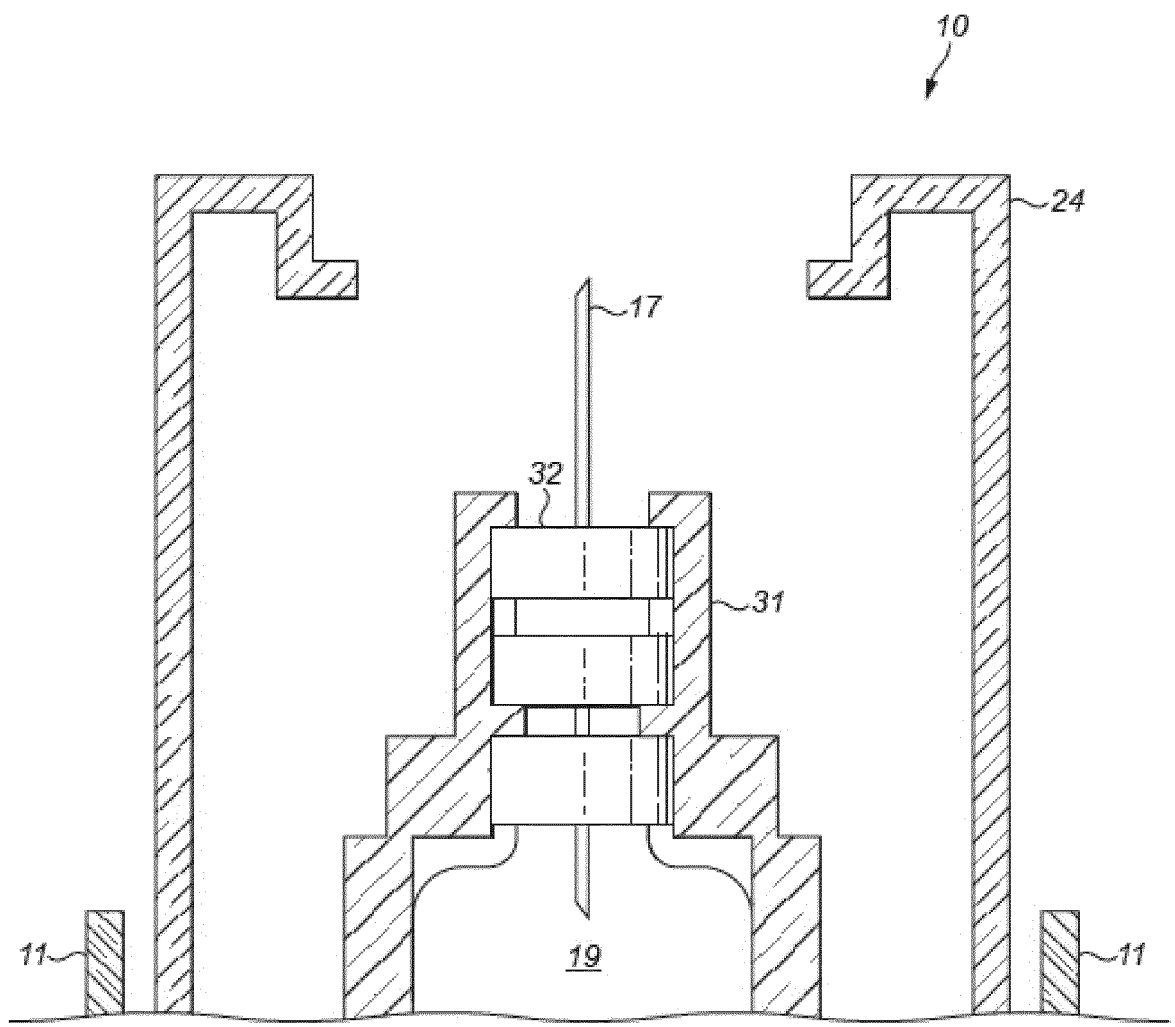
FIG. 5 is a cross sectional view of elements of the distal end of the auto-injector device at the stage shown in FIG. 2C.

FIG. 5 shows a cross sectional view of the distal end of the device 10 subsequent to the user removing the cap 12, corresponding to view in FIG. 2C. The cap 12 comprising the inner needle part 25 and the outer needle part 26 are removed together, thereby leaving the needle carrier 32 and needle 17 in place attached to the medicament cartridge 19. The needle sleeve 24 is movable with respect to the main body 11 of the device 10. The user may place the distal end of the device against the patient's injection site and then commence the injection.

While embodiments of the disclosure have been described with respect to auto-injectors, it should be borne in mind that the disclosure is also applicable to alternative injection devices, for example syringes, pen-injectors, manual injectors, spinal injection systems etc. The mechanism for attaching the needle to the medicament cartridge may be employed in any injection device 25 where it is desirable to keep the needle separate from the medicament until shortly before the injection.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, $15^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba@); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A medicament injection device comprising:
a main body configured to receive a medicament cartridge sealed by a penetrable barrier;
a cap assembly having an inner needle part and an outer needle part, wherein the inner needle part is movable in a proximal direction with respect to the outer needle part;
a needle carrier carrying a needle, the needle carrier being releasably coupled to the inner needle part;
a medicament cartridge holder configured to hold the medicament cartridge, the medicament cartridge holder comprising a needle carrier support part having a distal flange configured to support the needle carrier away from the medicament cartridge before displacement of the needle carrier and adapted to fix the needle carrier to the medicament cartridge subsequent to axial displacement of the needle carrier; and
a needle sleeve coupled to the cap assembly by a frictional fit, wherein, when the inner needle part is displaced in the proximal direction, the inner needle part causes the needle carrier to be displaced axially in the proximal direction, and wherein, subsequent to axial displacement of the inner needle part, the cap assembly is separable from the main body by movement of the cap assembly in a distal direction, and wherein the outer needle part comprises a ridge arranged to abut a flange of the needle sleeve so that movement of the cap assembly in the distal direction is prevented prior to displacement of the inner needle part in the proximal direction.

2. The medicament injection device of claim 1, wherein the needle carrier comprises a circumferential groove and the distal flange is arranged to engage with the circumferential groove so that the needle carrier is held away from, by an axial separation, the medicament cartridge prior to displacement of the needle carrier.

3. The medicament injection device of claim 1, wherein the inner needle part comprises a reinforcing flange configured to reinforce the outer needle part against the needle sleeve.

4. The medicament injection device of claim 1, wherein a proximal end and a distal end of the needle are each stored in respective substantially airtight compartments prior to proximal displacement of the inner needle part.

5. The medicament injection device of claim 1, wherein a distal end of the inner needle part comprises a tapered part arranged to engage with the outer needle part subsequent to axial displacement of the inner needle part in the proximal direction.

6. The medicament injection device of claim 5, wherein the tapered part is dimensioned to provide an audible feedback as the inner needle part is moved in the proximal direction.

7. The medicament injection device of claim 1, wherein the inner needle part comprises a shaded region to provide a visual indication to a user that the needle has not been inserted into the medicament cartridge.

8. The medicament injection device of claim 1, wherein the inner needle part comprises a transparent needle inspection portion.

9. The medicament injection device of claim 1, further comprising the medicament cartridge sealed by the penetrable barrier, wherein proximal axial movement of the needle carrier causes a proximal end of the needle to pierce the penetrable barrier.

10. The medicament injection device of claim 9, wherein the medicament cartridge contains a medicament.

11. The medicament injection device of claim 1, wherein the medicament injection device is an auto-injector device.

12. A method of operating a medicament injection device having a cap with a push button, the method comprising:
    abutting a ridge of an outer needle part of the cap with a flange of a needle sleeve of the medicament injection device so that movement of the cap in a distal axial direction is prevented prior to displacement of an inner needle part of the cap in a proximal axial direction;
    pushing the push button in the proximal axial direction, thereby causing:
        (i) a displacement of the inner needle part in the proximal axial direction with respect to the outer needle part;
        (ii) an axial displacement of a needle carrier from a first position to a second position, wherein in the first position the needle carrier is supported away from a medicament cartridge by a distal flange of a needle carrier support part of a medicament cartridge holder configured to hold the medicament cartridge, wherein in the second position the needle carrier is fixed to the medicament cartridge by the distal flange of the needle carrier; and
        (iii) a needle to pierce a penetrable barrier of the medicament cartridge; and
    pulling the cap in the distal axial direction to remove the cap from the medicament injection device.

13. The method of claim 12, wherein the needle comprises a proximal end and a distal end, and wherein the proximal end of the needle is configured to pierce the penetrable barrier of the medicament cartridge.

14. The method of claim 13, further comprising drawing a medicament from the medicament into the needle via the proximal end of the needle.

15. The method of claim 14, further comprising injecting the medicament into a patient via the distal end of the needle.

* * * * *